United States Patent
Zhang et al.

(10) Patent No.: US 7,795,035 B2
(45) Date of Patent: Sep. 14, 2010

(54) DETERMINATION OF CARBON NANOTUBE CONCENTRATION IN A SOLUTION BY FLUORESCENCE MEASUREMENT

(75) Inventors: Yuegang Zhang, Cupertino, CA (US); Shida Tan, Milpitas, CA (US); Herman Lopez, Sunnyvale, CA (US)

(73) Assignee: Intel Corporation, Santa Clara, CA (US)

( * ) Notice: Subject to any disclaimer, the term of this patent is extended or adjusted under 35 U.S.C. 154(b) by 1462 days.

(21) Appl. No.: 11/025,148

(22) Filed: Dec. 29, 2004

(65) Prior Publication Data

US 2006/0141634 A1    Jun. 29, 2006

(51) Int. Cl.
*G01N 33/00* (2006.01)
(52) U.S. Cl. .................. 436/172; 422/50; 422/68.1; 422/82.05; 422/82.08; 422/99
(58) Field of Classification Search .................. 422/50, 422/68.1, 82.05, 82.08, 99
See application file for complete search history.

(56) References Cited

U.S. PATENT DOCUMENTS

2004/0120880 A1    6/2004   Zhang et al.

OTHER PUBLICATIONS

Tan, Shida et al., "Optical Trapping of Single-Walled Carbon Nanotubes", Nano Letters, 2004, vol. 4, No. 8, pp. 1415-1419.

*Primary Examiner*—Sam P Siefke
(74) *Attorney, Agent, or Firm*—Buckley, Maschoff & Talwalkar LLC

(57) ABSTRACT

According to some embodiments, a method, a system, and an apparatus to determine a concentration of carbon nanotubes in a solution. In some embodiments, the method includes determining a photoluminescence intensity of a solution, mixing a sample of carbon nanotubes of an unknown concentration with the solution, determining a photoluminescence intensity of the mixture of the sample of carbon nanotubes and the solution, and determining a concentration of carbon nanotubes in the sample of carbon nanotubes based on the determined photoluminescence intensity of the mixture of the sample of carbon nanotubes and the solution.

16 Claims, 6 Drawing Sheets

DETERMINATION OF CARBON NANOTUBE CONCENTRATION IN A SOLUTION BY FLUORESCENCE MEASUREMENT

BACKGROUND

Carbon nanotubes (CNTs) have unique physical, electrical, and chemical properties. Depending on chirality and diameter, single-wall carbon nanotubes (SWNTs) have the characteristic of being either metallic or semi-conducting. For example, certain metallic carbon nanotubes may conduct electricity at room temperature, whereas semiconductor carbon nanotubes may not conduct electricity at room temperature.

A number of applications and potential uses have been proposed to exploit the unique properties of carbon nanotubes, including using carbon nanotubes in electronic devices. However, certain applications may require modification of the carbon nanotubes in order to render them functionally active for an application. Advances involving solubilization of individual SWNTs by surfactants or DNA oligomers in water provide possibilities regarding the application of carbon nanotubes.

The integration of carbon nanotubes into practical applications may require an understanding of the concentration of carbon nanotubes in a solution. Accordingly, the efficient application and usefulness of a solution containing carbon nanotubes may be limited without a determination of the concentration of carbon nanotubes in the solution.

DETAILED DESCRIPTION

The several embodiments described herein are solely for the purpose of illustration. Embodiments may include any currently or hereafter-known versions of the elements described herein. Therefore, persons skilled in the relevant art will recognize from this description that other embodiments may be practiced with various modifications and alterations.

Figure 1:
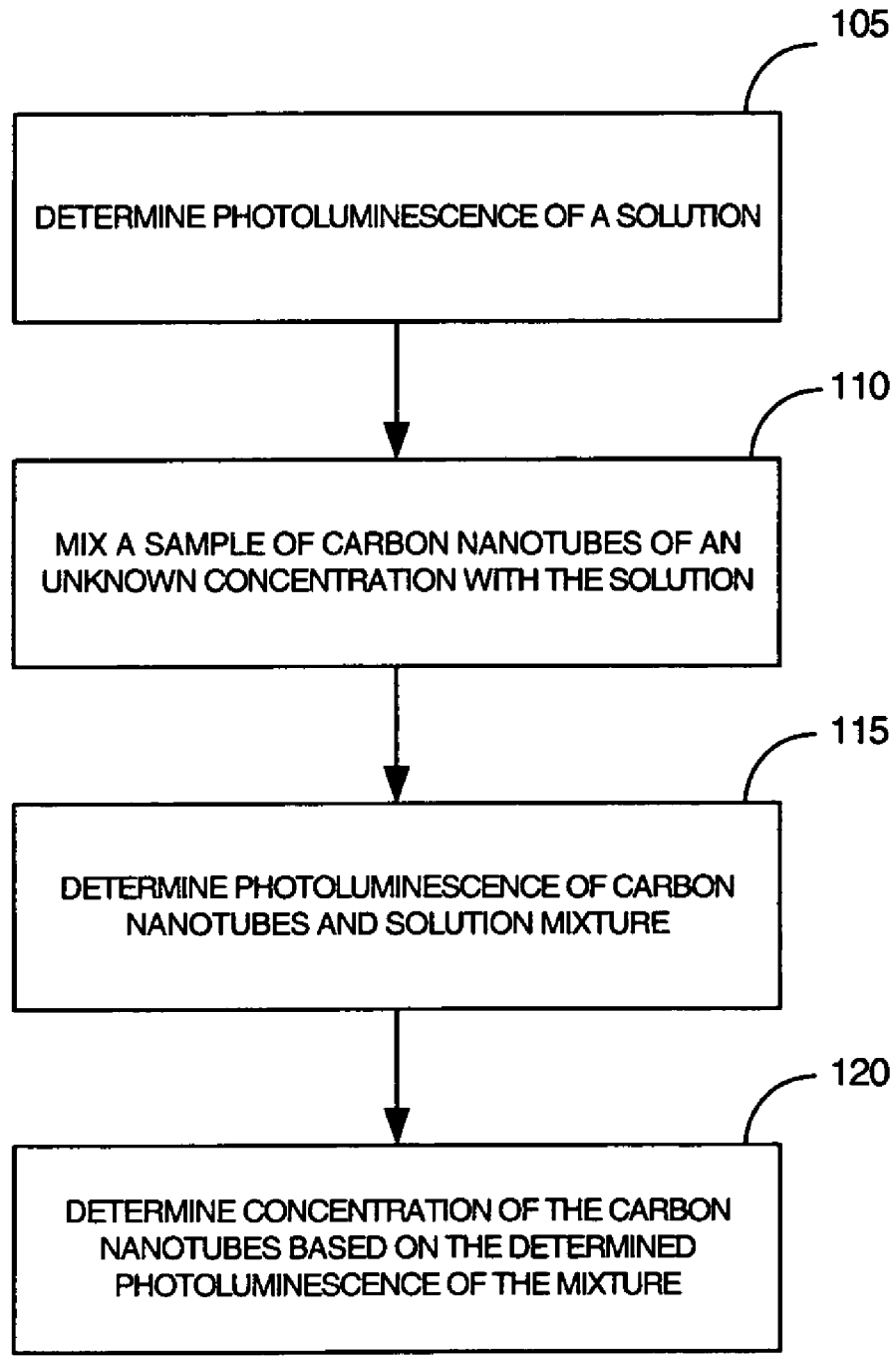
FIG. 1 is an exemplary flow diagram of a method, according to some embodiments hereof.

FIG. 1 provides an exemplary flow diagram of a process 100, used in some embodiments herein, to determine a concentration of carbon nanotubes in a solution. At operation 105, a photoluminescence intensity of a solution is determined. In some embodiments, the solution is free of carbon nanotubes. An example of a solution compatible with the methods herein includes, but is not limited to, a dye. The photoluminescence intensity of the solution may be induced by a variety of techniques and devices, including, for example, an excitation source having the output thereof focused on the solution. The photoluminescence intensity of the solution may be detected and determined in number of different manners, including those methods and devices that are now known or become known in the future.

At operation 110, a sample of soluble carbon nanotubes having an unknown concentration is mixed with the solution. Soluble carbon nanotubes, for example, water-soluble single-walled nanotubes, may be trapped (i.e., contained) and manipulated using a variety of manipulation techniques and devices. In some embodiments, optical tweezers may be used to trap a sample of carbon nanotubes, for mixing with a solution. The carbon nanotubes may be functionalized for mixing with the solution by, for example, surfactants or DNA oligomers in water. In some embodiments, a mixture may include a soluble SWNT sample functionalized with DNA oligomers and a TAMRA dye solution (SWNT-DNA-TAMRA). In some embodiments, a mixture may include a soluble SWNT sample functionalized with sodium dodecyl sulfate (SWNT-SDS) and a Rhodamine 6G dye solution.

At operation 115, a photoluminescence intensity of a sample of the mixture of carbon nanotubes and solution is provided. The determination of the photoluminescence intensity of the mixture may be obtained using a number and variety of photoluminescence determination techniques and devices. For example, the photoluminescence intensity of the mixture may be obtained using fluorescence microscopy.

At operation 120, a determination of the concentration of carbon nanotubes in the sample is obtained. The determination of the concentration of carbon nanotubes is based, at least in part, on the determined photoluminescence intensity of the solution, and the determined photoluminescence intensity of the mixture of carbon nanotubes and solution.

In some embodiments, a relationship between the photoluminescence intensity of the solution, and the photoluminescence intensity of the mixture of carbon nanotubes and solution forms a basis for the determination of the concentration of the carbon nanotubes. The relationship may be expressed as:

$$I_{PL} = A \cdot C_{CNT} + I_{PL}^0 \qquad (1)$$

where $I_{PL}$ is the photoluminescence intensity of the mixture of the sample of carbon nanotubes and the solution, A is a constant, $C_{CNT}$ is the concentration of the sample of carbon nanotubes, and $I_{PL}^0$ is the photoluminescence intensity of the solution free of carbon nanotubes.

Referring to process 100, the photoluminescence intensity of the solution, $I_{PL}^0$, may be determined at operation 105 and the photoluminescence intensity of the sample of the mixture of carbon nanotubes and the solution, $I_{PL}$, may be determined at operation 115. Having obtained the photoluminescence intensity of the solution, $I_{PL}^0$, and the photoluminescence intensity of the mixture of carbon nanotubes and solution, $I_{PL}$, the concentration of the carbon nanotubes, $C_{CNT}$, may be obtained at operation 120 based on equation (1).

In some embodiments, the value for the constant A may be obtained using a number of samples with different concentration of carbon nanotubes, each sample having a known concentration of carbon nanotubes therein. Given the known concentrations of a number of carbon nanotube samples and the photoluminescence intensity of a solution free of carbon nanotubes, $I_{PL}^0$, measured photoluminescence data may be used to determine a value for the constant A for a particular type of carbon nanotubes.

Figure 2:
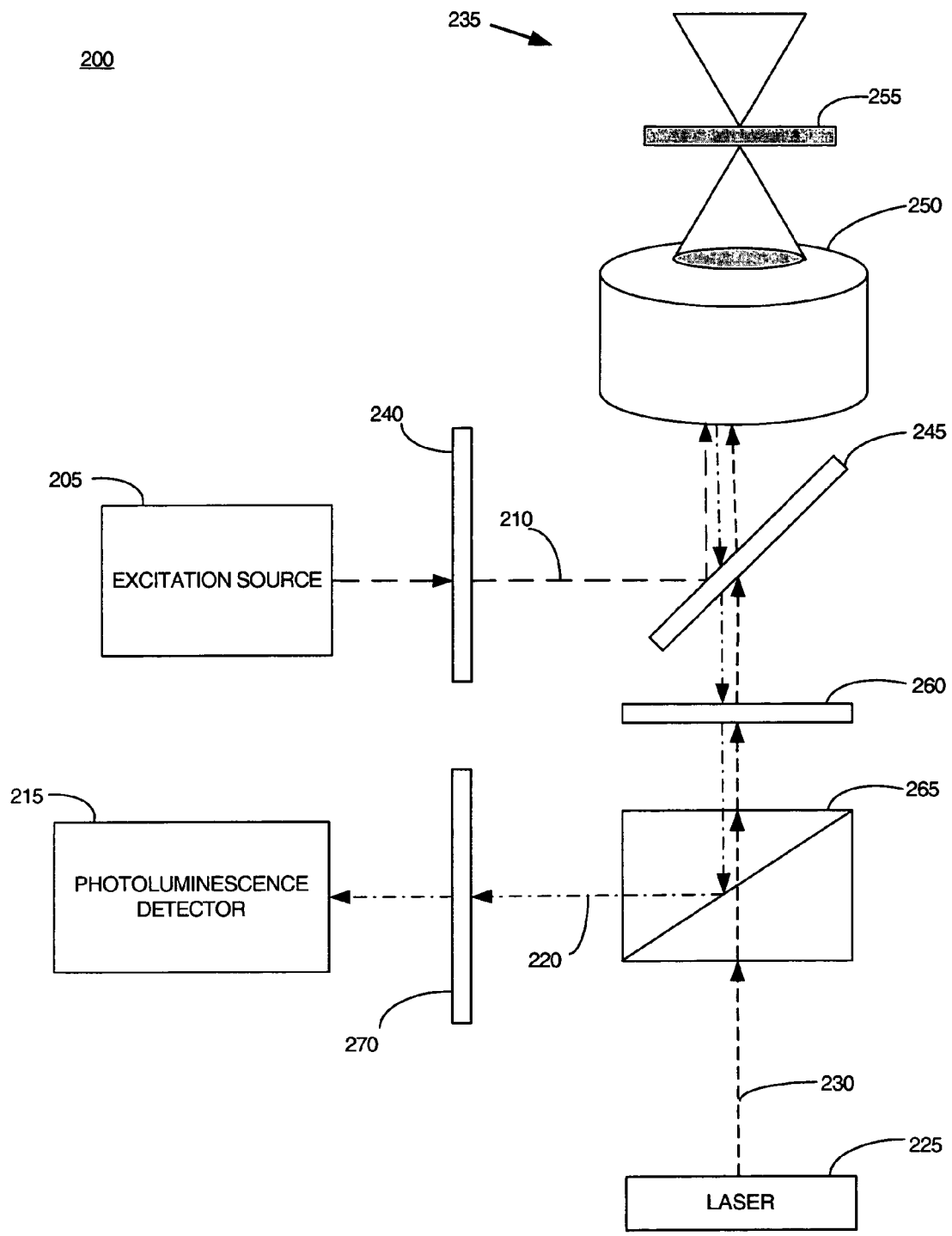
FIG. 2 illustrates an exemplary apparatus to determine a concentration of carbon nanotubes in a solution, according to some embodiments hereof.

In some embodiments, methods disclosed herein may be implemented using a variety of carbon nanotube manipulation devices and techniques, as well as a number of photoluminescence determining devices and techniques. FIG. 2 depicts an exemplary system 200 that may be used in accordance herewith. In some embodiments, a system or device may be modified to accomplish the functions to perform the methods disclosed herein. For example, a carbon nanotube manipulation device, such as an optical tweezers apparatus, may be used and/or modified to incorporate the functionality of system 200.

System 200 discloses a system for manipulating carbon nanotubes using optical tweezers. Those in the relevant art will appreciate and have knowledge of the construction, operation, and underlying principles involved in optical tweezers. Accordingly, details of the construction, operation, and underlying dynamics of optical tweezers are not discussed herein.

In some embodiments, system 200 includes an excitation source 205 that emits light 210, a photoluminescence detector 215 that detects photoluminescence 220, and a laser 225 that emits a laser beam 230 to trap carbon nanotubes in an optical trap 235. Excitation source 205 may include a light source such as, for example, a mercury lamp. Light 210 is provided to induce a photoluminescence in sample 255. Light 210 may be directed through an excitation filter 240 onto a dichroic filter 245. Excitation filter 240 may be provided to pass a specific spectrum of the light emitted by excitation source 205. Dichroic filter may be used, where necessary, to isolate certain regions of the light spectrum of light 210. From dichroic filter 245, the light passed thereby is focused by a microscope objective 250 onto a sample 255 in optical trap 235 to induce photoluminescence in the sample.

Laser beam 230 from laser 225 is directed to microscope objective 250. In some embodiments, laser 225 is directed through a beam splitter 265, an emission filter 260, and dichroic filter 245. In accordance with the principles and dynamics involved with optical tweezers (e.g., a momentum transfer associated with bending light), carbon nanotubes present in the sample 255 may be trapped and manipulated in optical trap 235 by laser 230.

As mentioned above, sample 255 is excited by light 210 to induce photoluminescence 220 in sample 255. The intensity of photoluminescence 220 is detected by photoluminescence detector 215. Emission filter 260 and infrared filter 270 may be provided, as needed, to condition the photoluminescence 220 for detection by photoluminescence detector 215. Photoluminescence detector 215 may be, for example, a charge-coupled device (CCD) camera, a spectrometer, or other light sensitive devices.

In accordance with other aspects herein, sample 255 may include a mixture solution of soluble carbon nanotubes (e.g., functionalized with, for example, SDS or DNA oligomers) and a solution (e.g., a dye).

Referring to FIGS. 1 and 2, excitation source 205 may be used to induce a photoluminescence in a solution free of carbon nanotubes and photoluminescence detector 215 may be used to determine the photoluminescence of the solution, per operation 105. Laser 225 and microscope objective 250, inter alia, may be used to trap and mix a sample of carbon nanotubes in the solution, according to operation 110. Photoluminescence detector 215 may be used to determine the photoluminescence of the mixture of carbon nanotubes and solution, in accordance with operation 115.

Those skilled in the art will recognize that the carbon nanotubes may be functionalized using a variety of techniques, including those now known and those that become known in the future. Those skilled in the art should also recognize that the optical tweezers system depicted in FIG. 2 is but one example of a carbon nanotube manipulation device and technique compatible with the present disclosure. For example, system 200 may include multiple lasers coupled into microscope objective 250, a high power infrared laser beam, a variety of lenses, mirrors, and acousto/electro-optical devices, and a connected computer to control and effectuate a precise steering of the carbon nanotube manipulation device (e.g., optical tweezers). Other carbon nanotube manipulation devices and techniques such as, for example, dielectrophoresis, surface anchoring and fluid manipulation in a microfluidic chip may be used in accordance with the present disclosure.

Applicants have realized that carbon nanotubes mixed with the solution exhibit fluorescence quenching. The fluorescence quenching effects of carbon nanotubes realized by Applicants were unexpected. For example, a soluble SWNT sample functionalized with DNA oligomers labeled by TAMRA dye (SWNT-DNA-TAMRA) has been observed to exhibit a decreased photoluminescence intensity, as compared to the photoluminescence intensity of the TAMRA dye solution alone.

Figure 3:
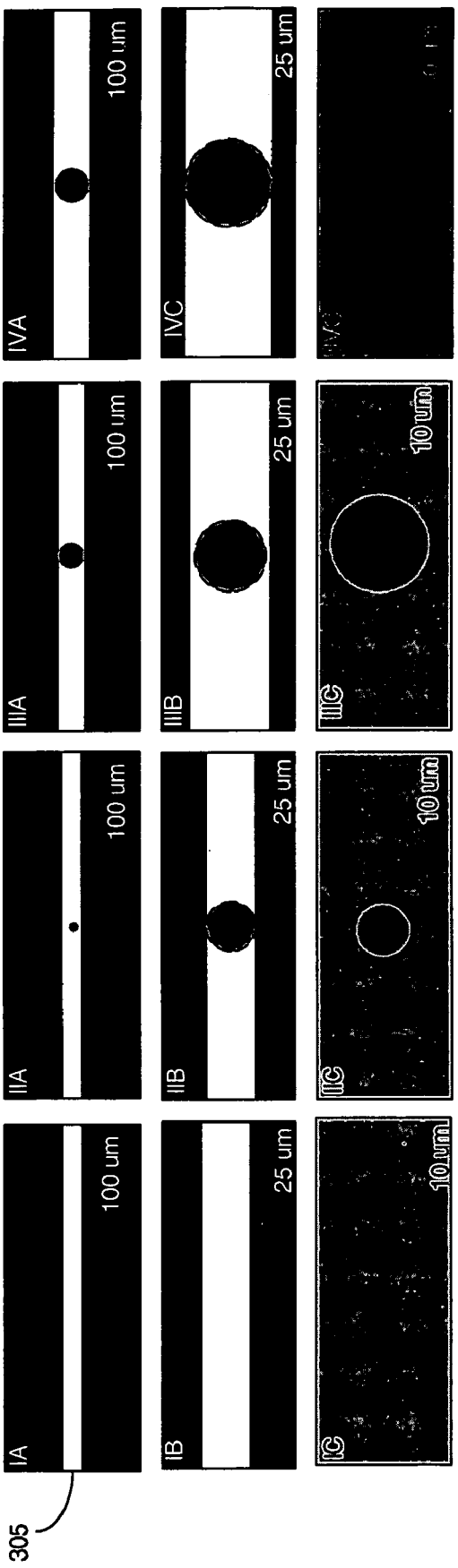
FIG. 3 is a depiction of exemplary photoluminescence images, in accordance with some embodiments hereof.

FIG. 3 illustratively depicts fluorescence images from a sample mixture of carbon nanotubes functionalized with DNA oligomers (CNT-DNA) and DNA-TAMRA solution in a 100 µm channel wide microfluidic channel. The images in rows A, B, and C are shown at 10×, 40×, and 100× magnification, respectively. The images shown in columns I and II have a 20 µm channel height, column II has a 40 µm channel height, and column IV has a 85 m channel height.

Column I depicts a fluorescence image of the CNT-DNA-TAMRA mixture with the optical trapping device turned off and should serve as a reference for the images in columns II, III, and IV. The dye in the mixture solution fluorescence, as made evident by the bright (i.e., fluorescent) column 305 in the image. As the magnification increases, moving from row A to row C, more of the fluorescent column is visible in the image.

The images illustrated in columns II, III, and IV depict florescence images of the CNT-DNA-TAMRA mixture with a carbon nanotube manipulation device optically trapping carbon nanotubes within the imaged column. As shown, a center "dark cloud" is present in the images of columns II, III, and IV. The "dark clouds" in the background photoluminescent column provides support that the carbon nanotubes trapped in the sample mixture quench the fluorescence of the DNA-TAMRA molecules attached to the carbon nanotubes. Applicants propose that DNA-TAMRA molecules that are not attached to carbon nanotubes provide the background photoluminescence shown in the images in columns II, III, and IV. Applicants have realized that fluorescence quenching due to free DNA-TAMRA molecules is not significant during trapping experiments in SWNT-DNA-TAMRA solution, and that a local decrease in fluorescence intensity may be primarily attributed to the quenching effect of SWNTs proximity to the free DNA-TAMRA moles. Accordingly, the "dark cloud" may provide an indication of the gathering of SWNTs by optical trapping.

Figure 4:
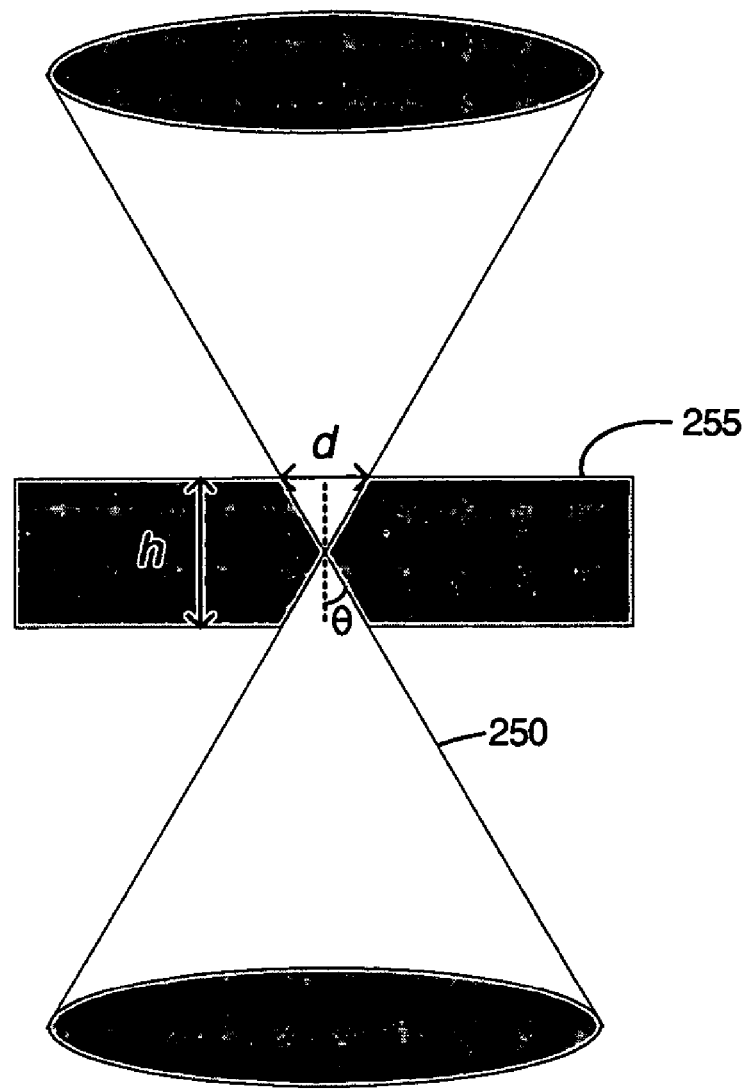
FIG. 4 is an exemplary illustration of an optical trap of FIG. 2, according to some embodiments hereof.

Referring to FIG. 3, it is shown that the size of the "dark cloud" increases as the channel height increases. The diameter of the irradiated area of the laser beam (e.g., 230) in the microfluidic channel is d=h tan θ, where h is the channel height and θ is the divergence angle determined by the numerical aperture of the microscope objective lens. A detailed view of the optical trap is shown in FIG. 4. Applicants have observed the calculated values for d in experiments. The calculated d values, represented as dotted circles in FIG. 3, substantially coincide with the "dark clouds" therein. As shown, the dark cloud substantially covers the entire irradiated volume of the laser beam (i.e., size of "dark cloud"=d).

Figure 5:
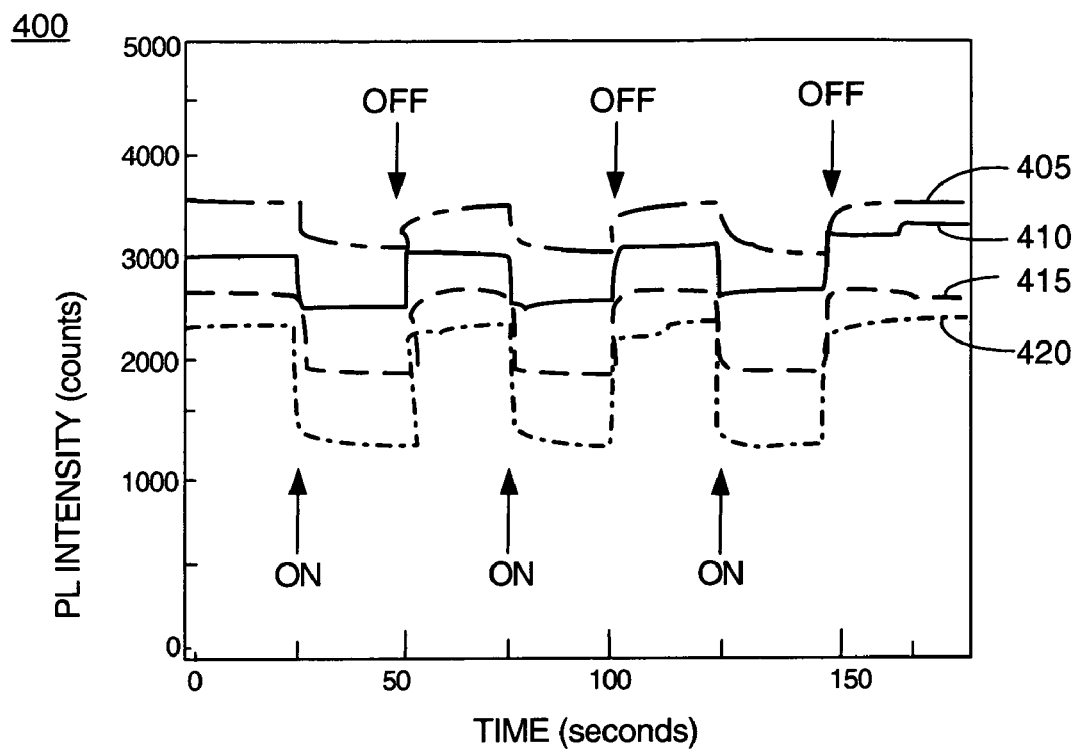
FIG. 5 is an exemplary depiction of a photoluminescence intensity measurement of a mixture of carbon nanotubes and solution monitored over a period of time as a trapping laser is cycled off and on, according to some embodiments hereof.

For a quantitative analysis of the fluorescence change due to SWNT trapping, a spectrometer or other photoluminescence detector may be used to study the photoluminescence intensity dependence on SWNT concentration. FIG. 5 shows four SWNT-DNA and DNA-TAMRA mixture solution samples, referenced 405, 410, 415, 420, prepared with a constant TAMRA concentration (0.003 µM) and different SWNT concentrations. FIG. 5 shows a photoluminescence peak intensity level of TAMRA (at 598 nm) from samples 405, 410, 415, and 420, monitored over time as a trapping laser (e.g., 225) is cycled on and off. A decrease of photoluminescence intensity level is shown when the trapping laser is turned on and a recovery of the photoluminescence intensity level is shown after the laser is turned off, corresponding to the formation and disappearance of the "dark cloud", as shown in FIG. 3. At time-zero (trapping laser off), the photoluminescence intensity level decreases with higher SWNT concentration, although all samples contain the same TAMRA concentration. This occurrence may be attributed to an increase of absorption and quenching of the TAMRA fluorescence by increasing the number of SWNTs. The dependence of photoluminescence intensity level on SWNT concentration can be used to explain the decrease of photoluminescence intensity level and to estimate the local SWNT concentration change when the trapping laser is turned on. During trapping (i.e., laser on), SWNTs are immediately drawn to the laser-irradiated volume, increasing the SWNT concentration surrounding the focus of the laser beam. The SWNT traveling speed under optical trapping can be roughly estimated to be 50-100 µm/s, about an order of magnitude higher than diffusion. This increase in local SWNT concentration causes the sharp reduction of photoluminescence intensity level. The photoluminescence intensity level continues to reduce as more SWNTs accumulate in the trapping volume. When the laser is turned off, the photoluminescence intensity level recovers to its original level due to restoration of individual SWNTs to their equilibrium concentration by, for example, Brownian motion. The photoluminescence intensity change by the trapping laser is directly related to the amount of trapped SWNTs (increase of local concentration).

Applicants have realized that the average SWNT concentration in the trapping area increased about from about 2 to about 4 times the original concentration. This was estimated by correlating the reduced photoluminescence intensity level during optical trapping to the interpolation of photoluminescence intensity level dependence on the SWNT concentration at time-zero. For example, the original concentration for sample 410 was 0.042 mg/mL. In FIG. 5, the photoluminescence intensity level from sample 410 at time-zero was 2759 counts. This photoluminescence intensity level reduced to 2168 counts when the optical trapping beam was turned on. From the photoluminescence intensity level concentration relationship established using the time-zero data, the reduced photoluminescence intensity level corresponds to a SWNT concentration of 0.15 mg/mL, which is about 3.6 times the original SWNT concentration. FIG. 5 shows a larger relative photoluminescence intensity change for samples with higher initial SWNT concentration. Therefore, more SWNTs can be trapped in solution of higher initial SWNT concentration.

Figure 6:
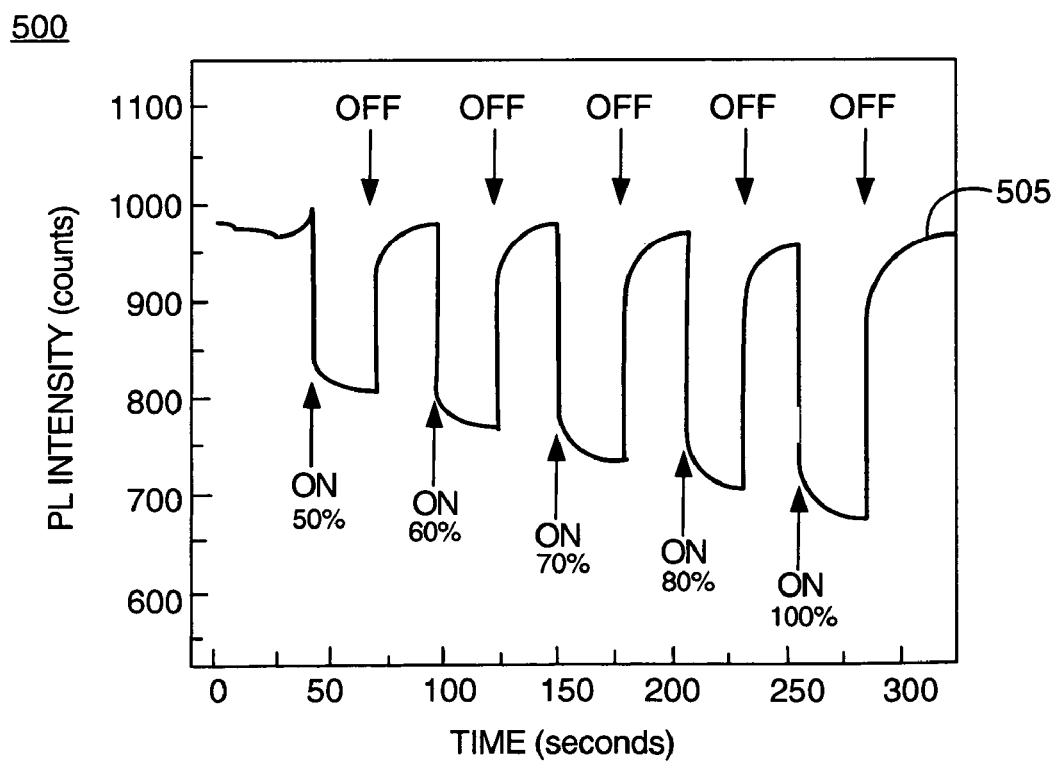
FIG. 6 is an exemplary depiction of a photoluminescence intensity measurement of a mixture of carbon nanotubes and solution monitored over a period of time and subject to an optical trapping laser having varying power, according to some embodiments hereof.

FIG. 6 illustrates an example of photoluminescence intensity measurements of a sample mixture with respect to varying trapping laser power. As shown, the trapping force is proportional to the gradient of laser intensity. That is, more SWNTs are trapped with a higher laser power under the same beam profile. As the power of the laser is increased from about 0 to about 300 mW, a threshold for optical trapping was observed at 100 mW.

Figure 7:
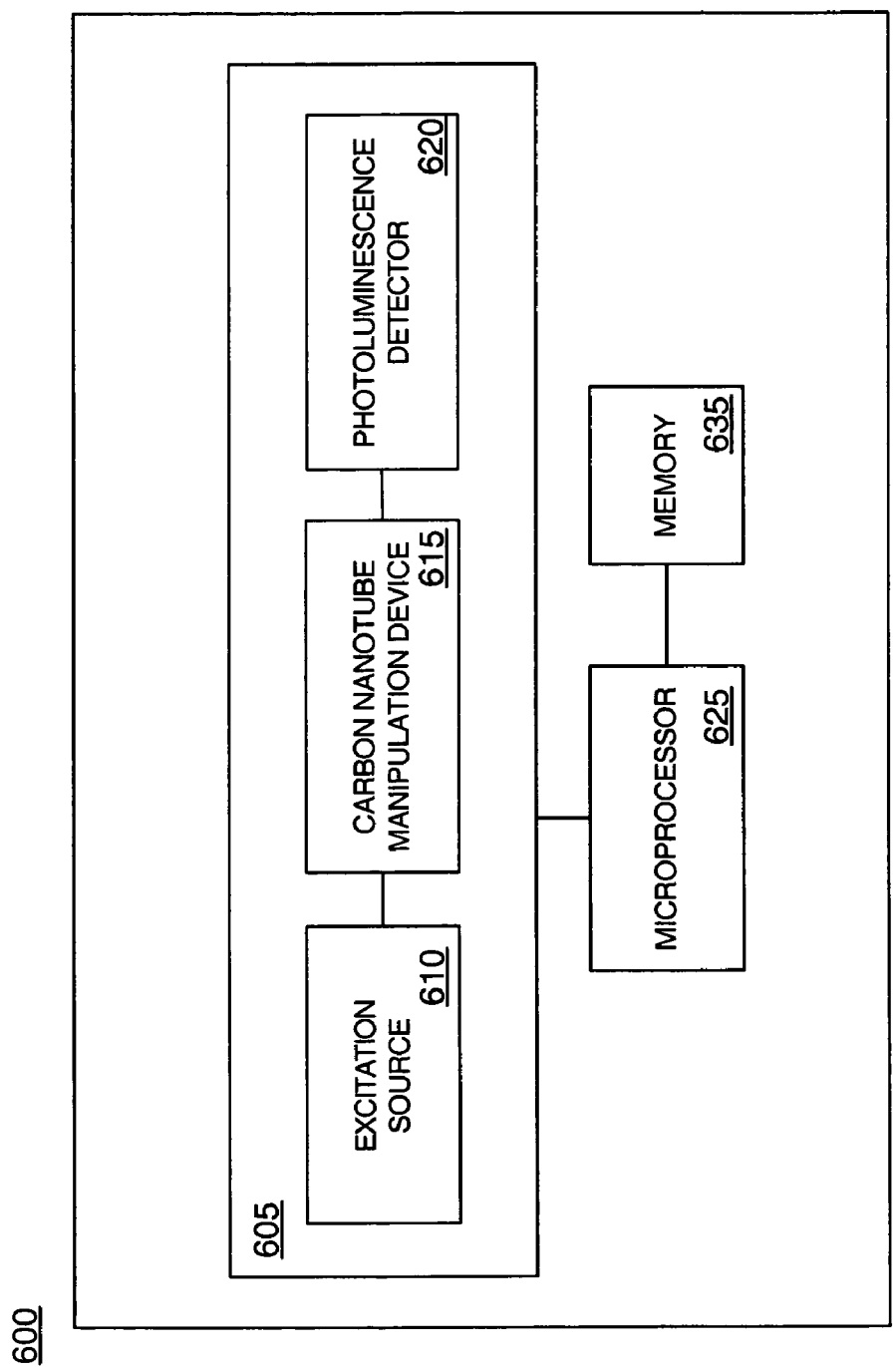
FIG. 7 is an exemplary system to determine a concentration of carbon nanotubes in a solution, in accordance some embodiments herewith.

FIG. 7 is a block diagram of a system 600 according to some embodiments hereof. System 600 may comprise components of a desktop computing platform. System 600 includes a carbon nanotube concentration determination device 605, a microprocessor 625, and a memory 630. Carbon nanotube concentration determination device 605 may include an excitation source 610 (e.g., a lamp), a carbon nanotube manipulation device 615 (e.g., optical tweezers), and a photoluminescence detector (e.g., a CCD). Those in the relevant art should appreciate that system 600 may include additional, fewer, or alternative components to microprocessor 625 and memory 625. Memory 625 may comprise any type of memory for storing data, including but not limited to a Single Data Rate Random Access Memory, a Double Data Rate Random Access Memory, or a Programmable Read Only Memory.

In operation, microprocessor 625 may control an operation or a sequence of operations of carbon nanotube concentration device 605. Memory 630 may be used to store instructions, that when executed by microprocessor 625, effectuate the methods of the present disclosure. The instructions may be part of a program, application, operating system, applet, routine, or any other arrangement of instructions executable by microprocessor 625. The methods implemented by system 600 may include the method illustrated in FIG. 1.

In some embodiments, microprocessor 625 may be used to control carbon nanotube concentration device 605 to determine the concentration of carbon nanotubes in a solution. Furthermore, the concentration of carbon nanotubes at a specific area, $I_{PL}(x,y)$, of a sample can be detected and determined by system 600. Microprocessor 625 may be used to precisely control the manipulation of the carbon nanotubes in a sample and to detect and determine the concentration of the carbon nanotubes therein. Accordingly, a photoluminescence intensity of an area, $I_{PL}(x,y)$, may be used in conjunction with equation 1 above to obtain a concentration distribution, $C_{CNT}(x,y)$, of carbon nanotubes in the sample.

Accordingly, in accordance with some embodiments hereof, various methods, devices, and systems to determine a concentration of carbon nanotubes in a solution have been discussed. The various methods, systems, and devices discussed herein may be used to increase the efficiency of determining the concentration of carbon nanotubes in a solution.

The several embodiments described herein are solely for the purpose of illustration. Persons in the relevant art will recognize from this description other embodiments may be practiced with modifications and alterations, limited only by the claims.

What is claimed is:

1. A method comprising:
   determining a photoluminescence intensity of a solution;
   mixing a sample of carbon nanotubes of an unknown concentration with the solution;
   determining a photoluminescence intensity of the mixture of the sample of carbon nanotubes and the solution; and
   determining a concentration of carbon nanotubes in the sample of carbon nanotubes based on the determined photoluminescence intensity of the mixture of the sample of carbon nanotubes and the solution.

2. The method of claim 1, wherein the solution is free of nanotubes.

3. The method of claim 1, wherein the solution is a dye.

4. The method of claim 1, wherein the carbon nanotubes are soluble.

5. The method of claim 1, wherein the carbon nanotubes are single wall nanotubes.

6. The method of claim 1, wherein the determining of a concentration of the carbon nanotubes in the sample of carbon nanotubes is based on the following:

$$I_{PL} = A \cdot C_{CNT} + I_{PL}^0$$

where $I_{PL}$ is the photoluminescence intensity of the mixture of the sample of carbon nanotubes and the solution, A is a constant, $C_{cNT}$ is the concentration of the sample of carbon nanotubes, and $I_{PL}^0$ is the photoluminescence intensity of the solution free of carbon nanotubes.

7. The method of claim 6, further comprising determining the constant A using a plurality of samples of carbon nanotubes having known concentrations.

8. The method of claim 6, wherein A is negative.

9. The method of claim 1, wherein the sample of carbon nanotubes is obtained by a carbon nanotube manipulation technique.

10. The method of claim 9, wherein the carbon nanotube manipulation technique is selected from the group consisting of: optical trapping, dielectrophoresis, surface anchoring, microfluidic flow manipulation, and combinations thereof.

11. The method of claim 1, further comprising exciting the solution and the mixture of the carbon nanotubes and the solution to induce photoluminescence therein, respectively.

12. The method of claim 11, wherein a source of the exciting is a lamp.

13. The method of claim 1, further comprising determining a concentration distribution of the carbon nanotubes in the mixture of the sample of carbon nanotubes and the solution.

14. An article, comprising:
a storage medium having stored thereon instructions that when executed by a machine result in the following:
determining a photoluminescence intensity of a solution;
mixing a sample of carbon nanotubes of an unknown concentration with the solution;
determining a photoluminescence intensity of the mixture of the sample of carbon nanotubes and the solution; and
determining a concentration of carbon nanotubes in the sample of carbon nanotubes based on the determined photoluminescence intensity of the mixture of the sample of carbon nanotubes and the solution.

15. The article of claim 14, wherein the solution is free of nanotubes.

16. The article of claim 14, wherein the solution is a dye.

* * * * *